June 1, 1937. J. D. BROWNELL Plant Pat. 248
ROSE
Filed May 9, 1936
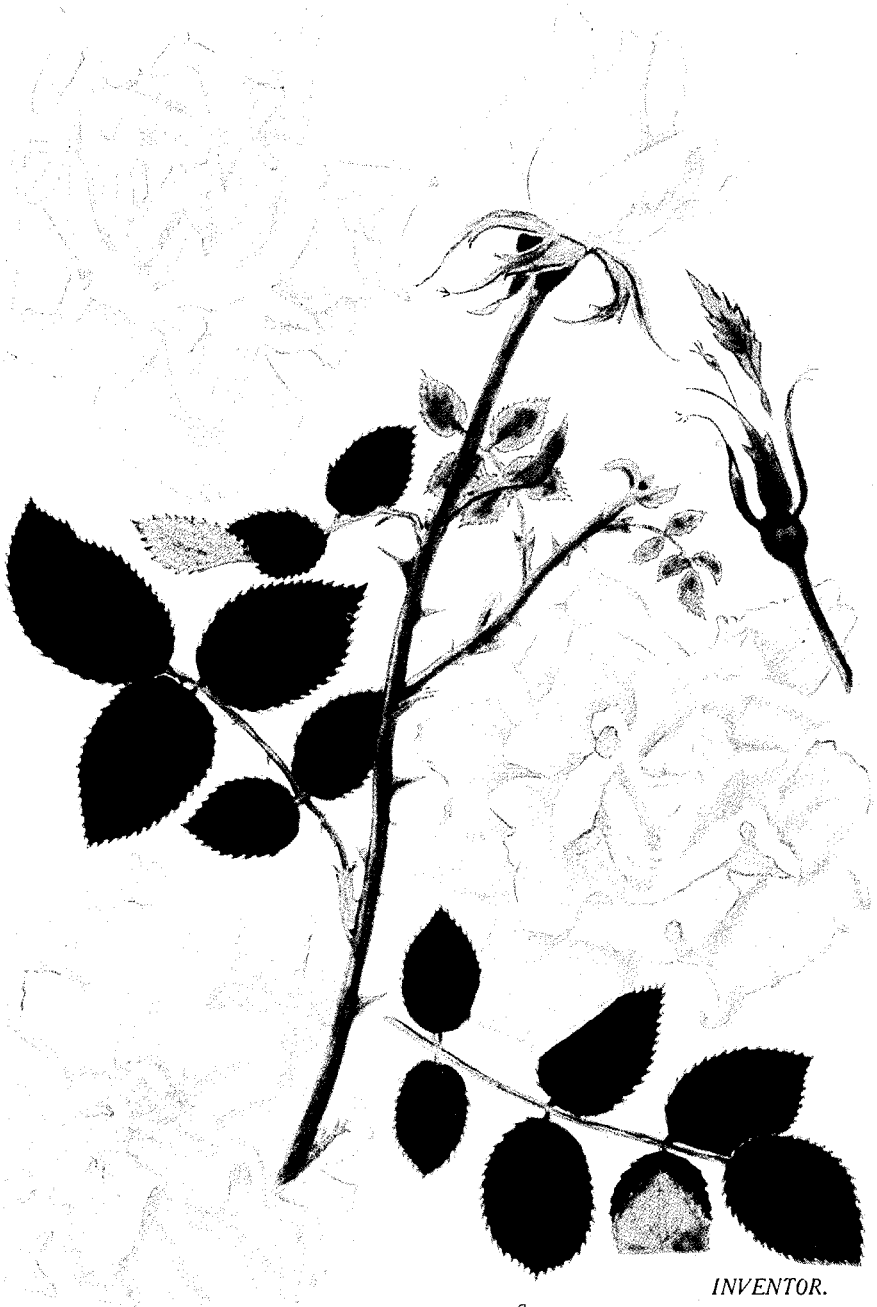
INVENTOR.
BY Josephine D. Brownell
ATTORNEY.

Patented June 1, 1937

Plant Pat. 248

UNITED STATES PATENT OFFICE

248

ROSE

Josephine D. Brownell, Little Compton, R. I.

Application May 9, 1936, Serial No. 78,768

1 Claim. (Cl. 47—61)

My invention relates to roses and especially to a new, original and distinct variety of the class known commercially as "hybrid teas", produced by me in my breeding grounds or garden by propagation, cross, self and open pollenation, which can be and has been asexually reproduced.

My new rose is new as to the following characteristics and especially as to their joint association in connection with the characteristics inherited from *Rosa wichuraiana,* of hardiness or immunity from serious injury on account of cold temperatures prevailing in certain parts of the northern United States:—

The unique, spectrum yellow, ordinary dictionary definition, to nearly spectrum yellow self color of its petals, the unusual brilliance and luster thereof and their tendency to hold this color under exposure;

The novelty and variation within certain definite limits of the form of the bloom and its character of holding that form for an unusually long time:—

Its intensity and character of fragrance, and

Its remontant and everblooming or reblooming habit, and

Its unusual intense expression of florescence, and

Its character of ascending in height by recurrent branching.

In the accompanying drawing forming a part of this specification I have shown my new rose in its natural colors, that is, as near as is possible to do so artificially.

I otherwise describe my new rose plant as follows:

In the accompanying drawing is shown a detached leaf with seven leaflets, which occasionally occurs on my rose plant and frequently on descendants of *Rosa wichuraiana,* but seldom on commercial forms of hybrid teas. My new rose plant is otherwise described as follows.

*Essential information*

*Type.*—Subzero hardy; dwarf to ascending to tall, for use in garden and greenhouse for cut flower, pot forcing and garden decoration.

*Class.*—Hybrid tea crossed with *Rosa wichuraiana.*

*Breeding or discovery.*—This rose plant was bred and discovered by me and under my directions, by propagation, cross, self and open pollenation. It is a seedling which was produced by open self pollenation, this procedure being used by me to recombine certain recessive and other factors, from a flower borne on a climbing rose produced by me at my breeding grounds in Little Compton, Rhode Island, said climbing rose was grown by me from a seed obtained by emasculation of a flower of the climbing rose "Mary Wallace", directed by me and protected from foreign and self pollen by a paraffin paper bag, hand pollenated with a camel's hair brush, and again similarly protected, the pollen used being from a hybrid tea rose grown by me for several years, the variety of said hybrid tea is known to me but not definitely identified by me as being a commercial variety and its parents and the maker of the parental cross being unknown to me. The source and history of this hybrid tea is as follows:—It came to me as a branch from a root stock or stem of a plant of Dr. Gahermit von Mitwig purchased by me from a leading rose nurseryman in or about the year 1920.

The date of the pollenation producing my new rose was July 5, 1931.* The seed was planted December 26, 1931, date of first flower was July 25, 1932.

*This and other dates herein are approximate.

My new rose plant and flower seem to me to be of unusual merit and I have since made extensive propagations thereof and tests of the variety.

Plants of this variety budded from this seedling on *Rosa multiflora* root stock, have entirely exposed to moderate subzero temperatures from zero Fahrenheit to twelve below zero, survived and bloomed normally the following season as hybrid teas. The plant has been propagated by budding at Little Compton, Rhode Island in the months of July in 1932–5 inclusive and the characters have successively reproduced, true to the original seedling.

*Flower*

*Habit.*—Blooms outdoors, beginning time about two days prior to average beginning time of commercial hybrid teas, and continues relatively to the growth of the plant until frost. In the greenhouse after two or three sets of blooms it, like most *Rosa wichuraiana hybrids,* tends to "rest" somewhat especially in the late winter.

*Flowers borne.*—One or frequently two or three and sometimes more on each stem, in regular hybrid tea type of cluster; peduncles, above the uppermost leaves are, medium in diameter and length, erect, light green, being frequently nearly Calliste green (this and other color plate reference herein not otherwise denoted are to Ridgway 1912 edition) Plate VI, almost smooth and usually free from prickles and bristles but with some small hairs. Stems are rather long, notably strong, diameter medium to small and of a notably hard, woody, stiff texture.

*Quantity of bloom.*—Is free to abundant, being cumulative in quantity of florescence from year to year as the plant increases in size and consequently a greater bloom quantity than most hybrid teas in commerce.

*Fragrance.*—Is strong China tea in combination with *Rosa wichuraiana,* under favorable environment.

*Bud.*—Has a normal neck, opens well, being but little to not at all affected by hot or wet weather or both, as to color and form, except at temperatures in excess of about one hundred degrees Fahrenheit, sufficiently prolonged, the petals occasionally tend to lose a portion of their rigidity.

Before calyx breaks the size is medium, form pointed to tapering, frequently with one or more sepals with foliaceous parts extending beyond the tips substantially one half inch and frequently with one broadly foliaceous sepal, the number and size of the foliaceous appendages being variable, and the sepals frequently having thread-like appendages, otherwise the sepals are usually normal and regular, tapering to nearly lanceolate near the apex, which turn back nearly perpendicular to the pedicle as the bud begins to open and later turn back more nearly parallel thereto.

Color of bud as calyx opens on both sides of petals, upper edges Pinard Yellow Plate IV, to one third toward Picric Yellow Plate IV, shading to Empire Yellow Plate IV, to one third toward Pale Lemon Yellow Plate IV, shading near the base to Lemon Yellow Plate IV, to Lemon Chrome Plate IV. The color intensity is slightly variable on blooms on the same plant and on different plants under different environment, the foregoing being a substantial average of that variability under favorable conditions; with notable brilliance and luster and unusually clear light center when sufficiently open to show anthers.

*Bloom.*—The rose is three and one half to five inches in diameter when fully open, infrequently more or less; double, having petals variable in number usually from twenty seven to thirty five, infrequently more or less. (It is to be noted that many varieties of H. T. crossed with *Rosa wichuraiana* in dwarf reblooming form, frequently have many characteristics with a wider range of variability than do the average of the present forms of commercial varieties of hybrid teas). The flower opens high centered, recurled, showing pistils and stamens somewhat, when fully open. It has a notable character of holding the center petals closed with three or four rows of petals held at various angles for an unusually long time. The petals are notably variable, from orbicular to obovate usually with inner petals more nearly ovate, outer petals usually recurled outward and frequently with warped edges sometimes crinkled, notched once at the center of the terminal edge, to slightly pointed, inner petals averaging narrower, to innermost petals frequently notably irregular to informal petaloids. Texture, medium to thick and leatherly, both sides slightly satiny to shiny with a metallic luster.

Color of opening flowers from plant budded January 1935 on potted *Rosa multiflora* root stock and grown in greenhouse in East Providence, Rhode Island, in four inch pots, picked May 21st same year, on opening, as compared with color charts in "The Rose Manual" by Doctor J. H. Nicolas 1930 edition, (which is here selected in preference to Ridgway because of the blended colors there shown comparing more accurately with the colors of the nearly selfed toned Lemon Yellow Ridgeway colors of my rose), is on one outside petal a small irregular splash of Scarlet Plate IV, about one inch above 3. This splash of Scarlet is typical and has obtained on one outside petal only on about half of the blooms grown to date. Otherwise the outer rows of petals were, outer side, upper portion, one third of area of petals Lemon, Plate I—Yellow Range at 2, center portion, Canary, about one inch below 1, lower portion Gold at 2, and intermediate areas shading variously between adjacent colors. Inside of outer row of petals, upper quarter Lemon at 2, next lower quarter Canary at 1, next lower quarter Gold at 2, lower quarter Saffron about one half inch below 1. These colors are diffused together and the mixture thereof changes gradually from one area described to the next. The inner rows of petals are of the same colors except that on the second row of petals on the outer side the Gold at the base is replaced by Saffron at 1, and the center is Gold at 2, and the upper portion is Canary at 1, on the inner side the Saffron and Gold areas are nearly similarly extended upward. On each successive inner row of petals the Gold and Saffron extend upward to a slightly increasing degree, the extreme inner row together with the petaloids when present in the center are Saffron both sides throughout. Flowers grown out of doors at Little Compton, Rhode Island, picked during June, July, August, September and October in the same year, compared very accurately with the above description and retain color similarly.

The color of the above described flowers after being five days in the house at temperatures from 60 to 75 degrees Fahrenheit, was outside petals, both sides terminal edges Straw at 3, Plate I, shading downward to Lemon at 2, to Canary at about one inch below 1, near the middle of the petals to Saffron about one and one half inches below 1, at the base of the petals, on each succeeding inner row in increasing proportions toward the center of the flower, extend the lower colors upward, the inner row of petals being Saffron about one inch below 1, and the petaloids slightly deeper Saffron. Color tone of the open center with anthers beginning to open at this period, in combination with the anthers, petaloids, top of the disc slightly showing and pistils and styles at this period is substantially Saffron at 1. The inner petals at this period are not all usually fully open. The single tone effect of the freshly opening flower is substantially Empire Yellow, Plate IV, Ridgway and has a marked brilliancy.

The petals are substantial and after three to five days drop off cleanly, usually of a bright yellow color with much of the brilliance remaining in wet or dry weather except that occasionally one or two petaloids or inner petals cling to turn dull yellow to fall later. The flower does not "ball" in wet weather at Little Compton, Rhode Island. The flower lasts well, is not affected at any stage by moderate cold or hot temperatures or humidity or wet weather.

*Reproductive organs.*—Stamens, quantity medium to many arranged regularly and are variable in number, are of uneven length, mostly 3/8 to 1/2 inch long, with Anthers, Light Salmon Orange, Ridgway, Plate II, Filaments, are Mustard Yellow, Ridgway, Plate XVI, Pistils are several, frequently from 45 to 50 of slightly uneven length approximating one half inch long, the Styles are Chalcedony Yellow, Ridgway, Plate XVII, the Stigmas are Citron Yellow, Ridgway, Plate XVI, the Pollen moderate in quantity, color Ivory Yellow, Ridgway, Plate XXX, the Ovaries usually all enclosed in hip.

Hips frequently develop, ovoid to globular with inconspicuous neck, green shading to russet and tending somewhat toward an overlay of red on the side exposed to sunlight, these color names are used in their ordinary dictionary definitions; moderately smooth walls moderately thin, fleshy. Size and shape closely resembling hips of Dr. W. VanFleet except somewhat flatter.

The sepals are persistent, some falling later, length moderate, nearly straight to bent downward near tip.

Seeds frequently averaging around six with about half apparently good embroys the other half shrivelled, none have germinated.

*Plant*

*Foliage.*—Is abundant to normal of compound leaves of usually three leaflets near the flower and five leaflets farther down the stem, and frequently seven leaflets near the base and occasionally a small single leaflet develops near the base of the rachis of five leafleted leaves. Size of leaflets moderately small to medium, moderately leathery and glossy. Forms of leaflets, round to slightly oval with the apex moderately acute, variable, the tip leaflet being usually slightly more acute, base rounded; on very short petiolules; margins slightly irregularly serrated. Color of leaflets on the upper surface is, grown out of doors, slightly variable from Dusky Yellowish Green, Ridgway. Plate XLI, to Dark Dull Yellow Green, Plate XXXII, and the reverse side is substantially Asphodel Green, Plate XLI. Under glass the colors are upper surface about intermediate between Dark Dull Yellow Green and Deep Dull Yellow Green (1), Plate XXXII, reverse Asphodel Green. The young growths more nearly compare with the colors of the stem to slightly brighter with edges of reddish tones shading from nearly Dark Indian Red, Plate XXVII, nearly to Dahlia Carmine, Plate XXVI, and somewhat lighter, with the red edges shading into greenish center areas, which replace the reddish colors as the leaflets develop.

Petioles and rachis are medium to short, moderately narrow to slender, upper side smooth except some very short reddish hairs, grooved. Under side, moderately smooth with some hairs and usually two to five short prickles, size from 4/16 to 1/16 inch long, in form similar to those on stems, of light green, tipped reddish.

Stipules are medium short averaging around 3/8 to 5/8 inch long, the width in center is about 3/16 inch, with relatively long narrow points, the upper edges of which when spread in the same plane make an angle of about 150 degrees.

Disease, resistant to mildew and blackspot.

*Growth.*—Habit dwarf becoming bushy. Its unusual way of developing is for some of the upper branches to become large and vigorous, then rebranch, thus developing a new hybrid tea type. This development increases the height of the plant approximately two feet a year in well grown specimens. The growth is moderately free at first, developing after one or two years under favorable vegetative opportunity extreme vigor, canes and branches, medium in the young plants developing in older plants variably from medium to very vigorous.

Main stems, color same as upper surface of leaves, shading variously to lighter and to more reddish and to color of pedicle. Prickles, several usually three to five between leaves, length averaging about 3/8 inch, bronze to red, shading from Dahlia Carmine, Ridgway, Plate XXVI, to lighter at the base turning lighter and dull later, with oval to elliptical base, tips arched usually very slightly downward, near the tips. Hairs several, red to green.

Very young branches color of prickles to lighter progressively and rapidly changing to color of main stem.

*Winter resistance.*—One of the outstanding characters of this variety is its resistance to certain subzero temperatures, in combination with the above described characters. It is to be noted that this is a hybrid tea rose plant descended in part from *Rosa wichuraiana.* This variety budded with the bud entirely exposed above ground to temperatures as low as about 23 degrees below zero Fahrenheit at Little Compton, Rhode Island survived and bloomed normally the following season. This plant so exposed to such subzero temperatures is affected thereby to the extent of at least a part of the stems and branches being injured and killed back. The growth of this plant in garden form, exposed to temperatures below ten below zero may be compared to the growth of garden forms of herbaceous peonies. This plant planted in the bed normally with the budded eye three inches below bed level, may under certain subzero exposure kill back to the ground, and normal growth from new eyes below ground will usually develop the plant by bloom time into a normal hybrid tea rose bush. This plant exposed to temperatures only above ten below zero will usually when well grown retain all or a substantial part of the branches and stems thereof in living condition and extend its growth upwards as above described.

*Longevity.*—As a natural consequence of the foregoing described characters the expected longevity of this plant is substantially greater than that of other forms of hybrid teas in commerce and in the opinion of the inventor from many tests and much data obtained, has the expectancy of being several times ten times as great as the average hybrid tea rose in commerce.

*Comparisons.*—In comparison with other yellow garden roses known to me this variety is more brilliant, and of a color more nearly spectrum yellow, having less red color in the tone of the petals and the open center is lighter and of more clear and brilliant yellow tones; this is notably true of such comparison with, Souv. de Claudius Pernet, Souvenir, Mrs. Erskine Pembroke Thom, Mrs. Pierre S. duPont, Sunburst and Golden Dawn, and of the center petals of Feu Pernet Ducher. None of these varieties or any other varieties in commerce, drops its petals at Little Compton, Rhode Island, with the color yellow so pure and brilliant as my new rose and in addition to the above comparisons in all cases my rose plant is differentiated by a distinct constitution with the seven leafleted leaves, the winter resistance, together with its character of branching and ascending due to vigorous growth from *Rosa wichuraiana* ancestry, of the upper branches, their winter survival and branches therefrom.

I claim:—

The rose substantially as shown and described, characterized by its new and distinctive constitution and especially by the pure yellow color of its petals, their brilliancy and luster, the clear light center of the bloom on opening, its extreme resistance to winter injury, its continuity and intensity of florescence, its intense and pleasing fragrance, its long keeping character of the color of its petals and the special form of its petals variable within certain definite limits, its character of holding that form, all in association with its habit of branching from bloom stems and from canes and stems from the base.

JOSEPHINE D. BROWNELL.